United States Patent
Satoh et al.

(10) Patent No.: US 10,238,232 B2
(45) Date of Patent: *Mar. 26, 2019

(54) SELECTIVE HYDROGEN ADDING EQUIPMENT FOR LIVING ORGANISM APPLICABLE FLUID

(71) Applicant: MIZ CO., LTD., Kanagawa (JP)

(72) Inventors: Fumitake Satoh, Kanagawa (JP); Tomoki Seo, Kanagawa (JP); Ryosuke Kurokawa, Kanagawa (JP); Bunpei Satoh, Kanagawa (JP)

(73) Assignee: Miz Co., Ltd., Kanagawa (JP)

( * ) Notice: Subject to any disclaimer, the term of this patent is extended or adjusted under 35 U.S.C. 154(b) by 460 days.

This patent is subject to a terminal disclaimer.

(21) Appl. No.: 14/851,994

(22) Filed: Sep. 11, 2015

(65) Prior Publication Data
US 2015/0374166 A1 Dec. 31, 2015

Related U.S. Application Data

(63) Continuation-in-part of application No. 13/566,884, filed on Aug. 3, 2012, now Pat. No. 9,149,774, which
(Continued)

(30) Foreign Application Priority Data

Jul. 15, 2011 (JP) .................................. 2011-156952

(51) Int. Cl.
*C02F 1/68* (2006.01)
*C01B 3/08* (2006.01)
*B01J 7/02* (2006.01)
(Continued)

(52) U.S. Cl.
CPC ........... *A47J 31/44* (2013.01); *B01F 3/04099* (2013.01); *B01F 3/04829* (2013.01);
(Continued)

(58) Field of Classification Search
None
See application file for complete search history.

(56) References Cited

U.S. PATENT DOCUMENTS 7,252,771 B2 8/2007 Kopinke et al.
7,534,275 B2 5/2009 Tonca
(Continued)

FOREIGN PATENT DOCUMENTS

CN  101142143 A   3/2008
EP    1867607 A1  12/2007
(Continued)

OTHER PUBLICATIONS

Machine translation for JP 2005-013925 A (Jan. 2005). Retrieved on Dec. 13, 2017.*
(Continued)

*Primary Examiner* — Jennifer A Leung
(74) *Attorney, Agent, or Firm* — Muncy, Geissler, Olds & Lowe, P.C.

(57) ABSTRACT

A selective hydrogen adding equipment for supplying hydrogen to a living organism applicable fluid includes a hydrogen generating system, that contains a hydrogen generating agent as an essential component, a hydrogen bubble forming implement, that stores the hydrogen generating system and has a gas/liquid separating section including a gas-permeable film or an open-close valve, and a closed container to accommodate the hydrogen adding equipment. The gas/liquid separating section vents hydrogen gas generated by a contact reaction between the hydrogen generating agent and water or water vapor, the gas/liquid separating section avoids the water from flowing out and/or avoids the living organism applicable fluid from flowing in. The gas/liquid separating section allows water vapor of the living organism applicable fluid to flow in the hydrogen bubble
(Continued)

forming implement so as to contact with the hydrogen generating agent.

7 Claims, 6 Drawing Sheets

Related U.S. Application Data is a continuation of application No. PCT/JP2012/061759, filed on May 8, 2011.

(51) Int. Cl.
- *A47J 31/44* (2006.01)
- *B01J 8/00* (2006.01)
- *B01F 13/00* (2006.01)
- *B01F 15/00* (2006.01)
- *B01F 15/02* (2006.01)
- *B01F 3/04* (2006.01)
- *C02F 1/70* (2006.01)

(52) U.S. Cl.
CPC .... *B01F 13/0022* (2013.01); *B01F 15/00512* (2013.01); *B01F 15/0224* (2013.01); *B01J 7/02* (2013.01); *B01J 8/00* (2013.01); *C01B 3/08* (2013.01); *C02F 1/68* (2013.01); *C02F 1/685* (2013.01); *C02F 1/687* (2013.01); *B01F 2003/04914* (2013.01); *C02F 1/705* (2013.01); *C02F 2307/02* (2013.01); *Y02E 60/36* (2013.01)

(56) References Cited

U.S. PATENT DOCUMENTS

| | | | | |
|---|---|---|---|---|
| 9,108,871 B2 * | 8/2015 | Satoh | | A23L 2/54 |
| 9,120,672 B2 * | 9/2015 | Satoh | | C01B 3/08 |
| 9,149,774 B2 * | 10/2015 | Satoh | | B01F 13/0022 |
| 2005/0036941 A1 | 2/2005 | Bae et al. | | |
| 2005/0121399 A1 | 6/2005 | Hayashi et al. | | |
| 2007/0128104 A1 | 6/2007 | Hayashi et al. | | |
| 2007/0221556 A1 | 9/2007 | Chung | | |
| 2008/0311225 A1 | 12/2008 | Shiga | | |
| 2010/0209338 A1 | 8/2010 | Miki et al. | | |
| 2011/0111048 A1 | 5/2011 | Satoh et al. | | |
| 2012/0087990 A1 | 4/2012 | Shiga | | |
| 2012/0225010 A1 | 9/2012 | Boyle et al. | | |

FOREIGN PATENT DOCUMENTS

| | | | |
|---|---|---|---|
| EP | 2508484 A1 | | 10/2012 |
| JP | 2002-172317 A | | 6/2002 |
| JP | 2004-041949 A | | 2/2004 |
| JP | 2004-243151 | | 2/2004 |
| JP | 2004-269323 A | | 9/2004 |
| JP | 2004243151 A | * | 9/2004 |
| JP | 2005-007380 | | 1/2005 |
| JP | 2005-013925 A | | 1/2005 |
| JP | 2006-255613 | | 9/2006 |
| JP | 2007-001633 | | 1/2007 |
| JP | 2007-134600 A | | 5/2007 |
| JP | 2007-167696 | | 7/2007 |
| JP | 2010-124808 A | | 6/2010 |
| JP | 2010-207802 | | 9/2010 |
| JP | 4652479 B1 | | 3/2011 |
| WO | WO-2010/103894 A1 | | 9/2010 |
| WO | WO-2012/056923 A1 | | 5/2012 |

OTHER PUBLICATIONS

European Search Report in application No. 12815085.1 dated Oct. 23, 2015 pp. 1-7.

* cited by examiner a.  a—1: Lampshade-like head part
    a—2: Axial part
    a—3: Flange b.  b—1: Center hole
    b—2: Fan-like hole
    b—3: Edge e-1: Hydrogen generating system
e-2: Cover material
e-3: Hydrogen bubble forming implement
e-4: Gas/liquid separating section f-1 : Tubular outer shell
f-2 : PET bottle
f-3 : Clarified water

SELECTIVE HYDROGEN ADDING EQUIPMENT FOR LIVING ORGANISM APPLICABLE FLUID

CROSS-REFERENCE TO RELATED APPLICATIONS

This application is a Continuation-in-Part of co-pending application Ser. No. 13/566,884, filed on Aug. 3, 2012, which is a Continuation of International PCT Application No. PCT/JP2012/061759 filed on May 8, 2011, for which priority is claimed under 35 U.S.C. § 120; and this application claims priority of Application No. 2011-156952, filed in Japan on Jul. 15, 2011 under 35 U.S.C. § 119; the entire contents of all of which are hereby incorporated by reference.

BACKGROUND OF THE INVENTION

1. Technical Field of the Invention

The present invention relates to a selective hydrogen adding equipment for living organism applicable fluid.

2. Description of the Related Art

As a method of producing living organism applicable hydrogen-contained fluid, known in the art are a method using a hydrogen water electrolytically generating apparatus for household use and a method causing metal pieces of metal magnesium as a hydrogen generating agent to contact with living organism applicable fluid (Japanese Patent Application Publication No. 2007-167696).

PRIOR ART DOCUMENT(S)

Patent Document(s)

[Patent Document 1] Japanese Patent Application Publication No. 2007-167696

SUMMARY OF THE INVENTION

Problems to be Solved by the Invention

In the case of obtaining living organism applicable hydrogen-contained fluid using hydrogen generating agent, the hydrogen generating agent may possibly change properties of the living organism applicable fluid when dissolving hydrogen molecules into the living organism applicable fluid. For example, if the hydrogen generating agent is metal magnesium, then magnesium ions are dissolved into the living organism applicable fluid to shift the pH thereof toward alkaline side in accordance with the following Formulae (1) and (2) when generating hydrogen.

$$Mg + 2H_2O \rightarrow Mg(OH)_2 + H_2 \quad \text{Formula (1)}$$

$$Mg(OH)_2 \rightarrow Mg^{2+} + 2OH^- \quad \text{Formula (2)}$$

However, it is not desirable in general to change, before and after the hydrogen generating reaction, constituents of the living organism applicable fluid having been already made up naturally or artificially. The change in constituents may in turn lead to altering the flavor of living organism applicable fluid, such as tea and mineral water.

Therefore, equipment for producing living organism applicable hydrogen-contained fluid is desired which does not change constituents of living organism applicable fluid.

Besides, only "food additives" are officially permitted as additives allowed for contacting with articles of food under the Food Sanitation Act.

Accordingly, when producing living organism applicable hydrogen-contained fluid using hydrogen generating agent, it violates the Food Sanitation Act to cause magnesium or hydrogenated product as the hydrogen generating agent to directly contact with living organism fluid.

Means for Solving the Problems

Through preparing a hydrogen generating system which contains a hydrogen generating agent such as metal aluminum or metal magnesium as an essential constituent, storing the hydrogen generating system in a hydrogen bubble forming implement having a gas/liquid separating section which is devised so as to release hydrogen gas while substantially not making water flow in, and/or to release hydrogen gas while substantially not making water flow out, and causing the hydrogen generating agent and generating-purpose water to react in the hydrogen bubble forming implement, the hydrogen gas generated from the hydrogen bubble forming implement is dissolved into living organism applicable fluid substantially without causing the generating-purpose water having been used for the hydrogen generating reaction to flow out into the living organism applicable fluid, thereby to solve the problems. Further, the hydrogen gas is supplied to a closed container gas phase section storing the living organism applicable fluid thereby to solve the problems. Furthermore, high pressure and high concentration hydrogen gas in the gas phase is dissolved into the living organism applicable fluid through shaking of the closed container, thereby providing high concentration or supersaturated living organism applicable hydrogen-contained fluid to solve the problems.

Advantageous Effect of the Invention

By supplying hydrogen into the living organism applicable fluid using such means, the living organism applicable hydrogen-contained fluid can be obtained without changing properties of the living organism applicable fluid. Moreover, using such means also allows high concentration hydrogen beverages to be easily produced without altering any flavor of beverages regardless of locations, such as home, workplace, street, and storefront.

DESCRIPTION OF THE PREFERRED EMBODIMENT

Figure 1A:
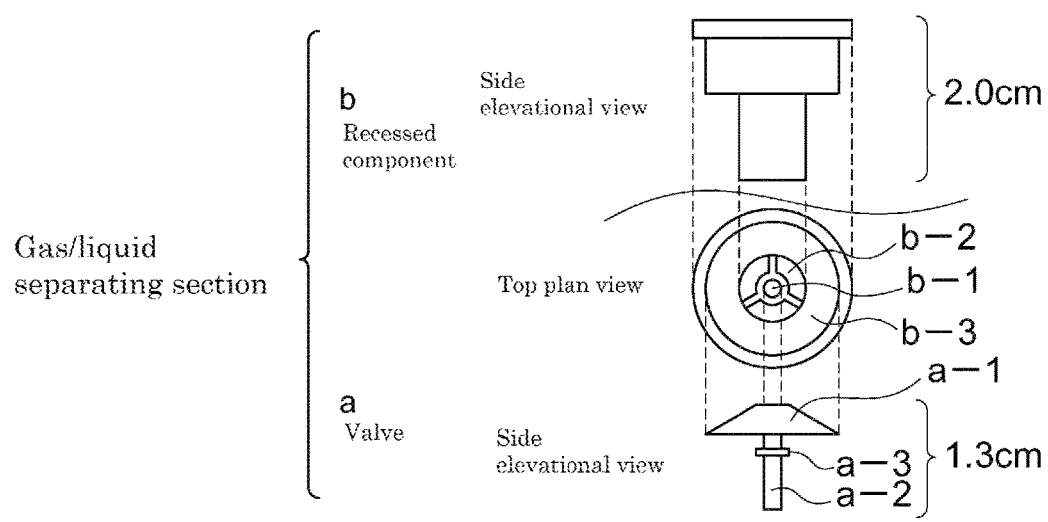
FIG. 1A depicts a plan view and front elevational views illustrating a gas/liquid separating section according to one embodiment of the present invention.

Hereinafter, embodiments of the present invention will be described.

Living organism applicable fluid in the present invention is a fluid to be applied to living organisms, such as water or water solution, which is an objective to be dissolved therein with hydrogen using the present invention. Examples of living organism applicable fluid include water as well as soft-drinks and beverages such as tea and coffee. Living organism applicable hydrogen-contained fluid to be obtained by dissolving hydrogen into the living organism applicable fluid is applied to living organisms via inhalation (atomization), drinking, injection, and the like, but is not limited thereto. While an active constituent of the living organism applicable hydrogen-contained fluid and high-concentration or supersaturated living organism applicable hydrogen-contained fluid is hydrogen and the functionality thereof is primarily inhibition of oxidative stress, the functionality is not limited thereto.

Hydrogen generating agent in the present invention is a substance which generates hydrogen. Examples of hydrogen generating agent include substances generating hydrogen by contacting with water, such as metals having higher ionization tendency than hydrogen and hydrogenated compounds including metal hydride. In consideration of the Food Sanitation Act and the safety of the resulting reaction products, it is preferred to use metals having higher ionization tendency than hydrogen (magnesium, aluminum, zinc, iron, cobalt, etc), which are food additives. Among them, metal aluminum is preferably used from the viewpoints of aesthetic aspect, cost, and safety in handling.

Generating-purpose water or water vapor in the present invention is a liquid or vapor for causing hydrogen gas to be generated in a hydrogen bubble forming implement through contacting with the hydrogen generating agent. Examples of such generating-purpose water or water vapor include tap water, clarified water, ion-exchanged water, purified water, pure water, RO water, their water vapor and the like, but are not limited thereto. The above-described living organism applicable fluid in itself or its vapor may also be used as the generating-purpose water or water vapor. Regardless of contained components, hardness, and liquid properties, any liquid or vapor including water or water vapor may be used as the generating-purpose water or water vapor in the present invention.

The hydrogen bubble forming implement of the present invention is characterized by isolating the hydrogen generating system from the living organism applicable fluid and delivering hydrogen gas, which has been generated in the hydrogen bubble forming implement, to the living organic applicable fluid via a gas/liquid separating section of the hydrogen bubble forming implement. The equipment of the present invention including the hydrogen bubble forming implement can be accommodated in a closed container so as to be a separate apparatus from the closed container for accommodating it or to be a structural site incorporated in the closed container.

Such a gas/liquid separating section is characterized, for example, by being devised such that a valve (such as a check valve or a ball valve), a gas permeable film (such as anion-exchange membrane or cation-exchange membrane) or the like is included as a component or material thereby to vent hydrogen gas generated by the contact reaction between the hydrogen generating system and the generating-purpose water and to substantially avoid the generating-purpose water from flowing out and/or avoid the living organism applicable fluid from flowing in. The water vapor of the living organism applicable fluid, however, can flow in the hydrogen bubble forming implement through the gas/liquid separating section. The water vapor causes hydrogen gas to be generated in a hydrogen bubble forming implement through contacting with the hydrogen generating agent.

Such devising includes providing an equipment for producing living organism applicable hydrogen-contained fluid, which has a hydrogen bubble forming implement provided with a gas/liquid separating section having a gas-permeable film which is poorly-permeable or non-permeable for water and permeable for hydrogen gas and of which material (fabric, paper, plastic, rubber, ceramic, etc) and thickness are not limited, wherein the equipment for producing living organism applicable hydrogen-contained fluid is characterized in that the hydrogen generating system or its hydrogen generating agent is processed for thermal insulation and, if necessary, the hydrogen bubble forming implement is processed for heat retention. Further, the equipment according to the present invention may also be devised to have an opening and closing section capable of opening and closing the gas/liquid separating section or a part of the hydrogen bubble forming implement, thereby allowing the hydrogen generating system and the generating-purpose water to be put into the hydrogen bubble forming implement via the opening and closing section.

Here, the thermal insulation process for the hydrogen generating system or the hydrogen generating agent therein is aimed at suppressing the increased reaction heat caused by the grain form of the hydrogen generating agent, which is employed for the reason of facilitating the hydrogen generating reaction. Examples of such process include, such as, but not limited to, covering by a cover material the hydrogen generating system or the hydrogen generating agent therein, tableting or solidifying the hydrogen generating system or the hydrogen generating agent therein, and forming a fireproof layer through the generation of by-products due to the hydrogen generating reaction.

In addition, the thermal insulation process in the present invention also includes using as the hydrogen generating agent a metal raw material of which the exothermic reaction is moderate or less.

Here, the cover material is operative: to maintain portions of the hydrogen generating system in a status where the portions are adjacent to each other thereby to enhance the efficiency of the hydrogen generating reaction; to prevent the reaction heat during the hydrogen generating reaction from directly transferring to the gas-permeable film of the gas/liquid separating section thereby to avoid the deterioration and degradation of the gas-permeable film; and, in the case that the hydrogen generating system has pH adjuster, to avoid the degradation of the gas-permeable film caused from the acidity or alkalinity thereof. In addition, the cover material also has a feature that it is permeated with hydrogen gas and water but is not permeated with the hydrogen generating agent and reaction residues thereof. Therefore, it is desirable that the pore size of the cover material is 1,000 μm or less, preferably 500 μm or less, more preferably 150 μm or less, and most preferably 50 μm or less.

Here, tableting or solidifying is aimed at employing compression forming (tablet forming) possibly in combination with appropriate diluents thereby to optimize the balance between the efficiency of the hydrogen generating reaction caused by the hydrogen generating system or the hydrogen generating agent therein and the suppression of the reaction heat. Even if a metal is used as the hydrogen generating agent, the above-described method may tablet or solidify metal grains or powder of that metal thereby to suppress the reaction heat during the hydrogen generating reaction while ensuring enough surface area for contributing to the reaction. For example, if such tableting or solidifying is performed by tablet forming, in order to ensure certain spaces among grains and to increase the surface area while avoiding shape losing, it is desirable that the tableting pressure is, such as, but not limited to, within the range from 0.1 kN to 100 kN, preferably 0.3 kN to 50 kN, more preferably 0.5 kN to 20 kN, and furthermore preferably 0.5 kN to 10 kN. In addition, such tablets or solidified materials may also be held in one or more further cover materials.

Here, forming a fireproof layer through the generation of by-products due to the hydrogen generating reaction is intended to include, such as, but not limited to, avoiding the probability of heat generation due to metal aluminum possibly even remaining after the hydrogen generating reaction, using the fire-resistance of alumina cement as the reduction product in the hydrogen generating reaction where the hydrogen generating system includes metal aluminum as the hydrogen generating agent and calcium oxide or calcium hydroxide as the pH adjuster.

Here, using a metal raw material of which the exothermic reaction is moderate or less is using a metal raw material characterized in that the temperature thereof is below 50 degrees C. when measured by a "metal raw material heat generation temperature measurement method" as will be described hereinafter or the metal raw material requires 5 seconds or more before reaching 50 degrees C. if exceeding 50 degrees C.

The "metal raw material heat generation temperature measurement method" is a method for measuring the temperature of an arbitrary metal raw material when causing a hydrogen generating system, which is comprised of the metal raw material 500 mg and malic acid (DL-malic acid: FUSO CHEMICAL CO., LTD., for example) 500 mg, to react with tap water (Fujisawa city tap water, for example) 500 mg of water temperature 25 to 26 degrees C. as the generating-purpose water in a polypropylene test tube of about 16.0 mL volume and about 17×100 mm (Test Tube with 2-position Cap, 17×100 mm, 16.0 mL volume, Total Length: 100 mm, Outer Diameter: 16.5 mm, Inner Diameter: 15 mm, Cap Size: 20.0×17.5 mm, catalog No. 222-2393-080 available from BM Equipment Co., Ltd., for example). Note that, if the metal raw material is aluminum as being amphoteric metal, then aluminum potassium sulfate (aluminum potassium sulfate: Wako Pure Chemical Industries, Ltd., for example) may be used as alkaline agent.

Specifically, the measurement of temperature of metal raw material includes disposing the above hydrogen generating system in a polypropylene test tube of about 16.0 mL volume and about 17×100 mm, then closing it with a cap, and injecting the generating-purpose water using a dropper from a cap opening (an opening of 5 mm diameter herein) previously provided at the center area of the cap. Immediately thereafter, a previously warmed-up digital thermometer (TANITA TT-508: TANITA Corporation) is inserted deeply into the inside of the test tube to contact the thermometer heat sensor unit (4 mm diameter herein) with the metal raw material thereby performing the measurement. Note that, if the diameter of the cap opening and the diameter of the thermometer heat sensor unit is the same, then the cap may possibly fly away due to hydrogen gas generated in the tube, so a space of about 1 mm may have to be provided between the cap opening and the thermometer heat sensor unit.

If using a metal raw material of which the exothermic reaction is moderate or less, i.e. the temperature thereof is below 50 degrees C. when measured by such a "metal raw material heat generation temperature measurement method" or the metal raw material requires 5 seconds or more before reaching 50 degrees C. in the case of exceeding 50 degrees C., then the extent is relatively small where the high-temperature metal raw material may fly away with the generating-purpose water during the exothermic reaction (hydrogen generating reaction). If, however, using a metal raw material of which the exothermic reaction is severe, i.e. the temperature thereof reaches 50 degrees C. within 5 seconds, then the high-temperature metal raw material may fly away with the generating-purpose water during the exothermic reaction (hydrogen generating reaction) and probably adhere to the gas/liquid separating section or the inner wall of the hydrogen bubble forming implement, so it is not preferred for the thermal insulation process in the present invention.

Moreover, if the exothermic reaction is gentle such that reaching 50 degrees C. requires 5 seconds or more, then there is an additional merit in handling the equipment that users of the present invention can release the equipment into the living organism applicable fluid container before they physically sense the significant heat generation of the equipment itself associated with the exothermic reaction.

Note that the metal raw material to be preferably used in the present invention may not be unambiguously defined in terms of the grain diameter or surface area of the metal raw material because there are many cases that the metal raw material to be used in the present invention is commercially produced as a powder-like product including various grain diameter distribution or a tape-like product appropriately processed to be stretched.

As metal elements for providing the metal raw material, among lithium, potassium, calcium, sodium, magnesium, aluminum, manganese, zinc, chrome, iron, cadmium, cobalt, nickel, tin, and lead which are metals having higher ionization tendency than hydrogen, metals not having unduly high ionization tendency and having good handling ability, such as magnesium, aluminum, manganese, zinc, iron, cobalt, and nickel, are preferably used. Among them, magnesium, aluminum, zinc, iron, and cobalt are particularly preferable because the safety thereof for living organism is high. Note, however, that the same metal element may be such that "the exothermic reaction is moderate or less" or may be alternatively such that "the exothermic reaction is severe" depending on the form of the metal raw material, and therefore, the metal raw material to be preferably used in the present invention may not be unambiguously defined in terms only of the metal element.

Therefore, when the thermal insulation process in the present invention employs a method "using a metal raw material of which the exothermic reaction is moderate or less", it is preferred that an available metal raw material is appropriately determined by the above "metal raw material heat generation temperature measurement method".

It should be noted that the merit is obtained where an available metal raw material may be selected by the "metal raw material heat generation temperature measurement method" so as not to necessarily require the previously described other thermal insulation processes, such as "covering by a cover material", "tableting or solidifying", and "forming a fireproof layer through the generation of by-products due to the hydrogen generating reaction".

It should also be noted that various types of such thermal insulation processes are effective even in the case where a valve is used for the gas/liquid separating section.

Besides, the heat retention process for the hydrogen bubble forming implement herein is aimed at smoothly progressing the hydrogen generating reaction in the hydrogen bubble forming implement through buffering the direct contact between the hydrogen bubble forming implement and the living organism applicable fluid existing outside thereof to suppress the hydrogen bubble forming implement from being cooled by the living organism applicable fluid.

Examples of such heat retention process include, such as, but not limited to, imparting an appropriate thickness to the outer wall of the hydrogen bubble forming implement or covering with an outer shell the periphery of the hydrogen bubble forming implement and, if necessary, providing an appropriate air layer between the hydrogen bubble forming implement and the outer shell thereby to prevent the heat from escaping directly from water.

Although not limited to, it is desirable that the thickness of the hydrogen bubble forming implement is 0.1 mm or more, preferably 0.5 mm or more, and further preferably 1.0 mm or more. The air layer provided between the hydrogen bubble forming implement and the outer shell is such that, but not limited to, the distance therebetween is desirable to be 0.1 mm or more, preferably 0.5 mm or more, and further preferably 1.0 mm or more.

For example, in a hydrogen generating system containing aluminum as the hydrogen generating agent and alkaline agent, such as calcium oxide or calcium hydroxide, which is a food additive, as the pH adjuster as will be described later, the reaction rate of the hydrogen generating reaction significantly varies depending on the water temperature of the living organism applicable fluid contacting the hydrogen bubble forming implement in which the hydrogen generating system is stored. More specifically, when the water temperature of the living organism applicable fluid is 4 degrees C., the hydrogen generating reaction considerably slows down compared to the case where the water temperature is 20 degrees C., whereas on the other hand, even if the water temperature of the living organism applicable fluid is 4 degrees C., on the occasion that the heat retention of the hydrogen bubble forming implement is appropriately promoted such as by covering with an outer shell the periphery of the hydrogen bubble forming implement and providing an appropriate air layer, the hydrogen generating reaction comes to be faster than the case of no heat retention.

Therefore, in the present invention, it is preferred in general that the hydrogen bubble forming implement is subjected to heat retention process in order to reduce the time duration until when the living organism applicable fluid will contain sufficient amount of hydrogen molecules.

It should be noted that such heat retention processes are effective even in the case where a valve is used for the gas/liquid separating section.

Similarly, it is further desirable that the hydrogen generating system contains exothermic agent for facilitating the hydrogen generating reaction.

For example, in a hydrogen generating system containing aluminum as the hydrogen generating agent and calcium oxide as the pH adjuster, a heat of hydration while calcium oxide is hydrated with the generating-purpose water to generate calcium hydroxide may be utilized for the hydrogen generating reaction caused by aluminum and calcium hydroxide. In this case, calcium oxide acts not only as the pH adjuster but as the exothermic agent. Therefore, even in the case where the hydrogen generating system contains aluminum as the hydrogen generating agent and calcium hydroxide as the pH adjuster, it is preferred to further contain calcium oxide as the exothermic agent.

In addition, another embodiment of the present invention involves, for example, providing a valve in the gas/liquid separating section to prevent the living organism applicable fluid from flowing into the hydrogen bubble forming implement. This allows for preventing water having flowed into the hydrogen bubble forming implement from flowing out again to the living organism applicable fluid during the shaking and the like, while the hydrogen gas generated in the hydrogen bubble forming implement is capable of being released into the living organism applicable fluid. More specifically, such a valve provided in the gas/liquid separating section is an open-close type valve which separates the internal and external of the hydrogen bubble forming implement, and which is to be opened by a gas pressure of the hydrogen gas generated in the internal of the hydrogen bubble forming implement owing to the reaction between the hydrogen generating system and the generating-purpose water thereby to exhaust the hydrogen gas into the external of the hydrogen bubble forming implement, while to be naturally or artificially closed after the exhaust through the gravity force or the water pressure from the external of the hydrogen bubble forming implement. The valve is characterized by substantially not causing the organism-applicable fluid existing at the external of the hydrogen bubble forming implement to flow into the internal thereof except for during the exhaust of the hydrogen gas.

Figure 1B:
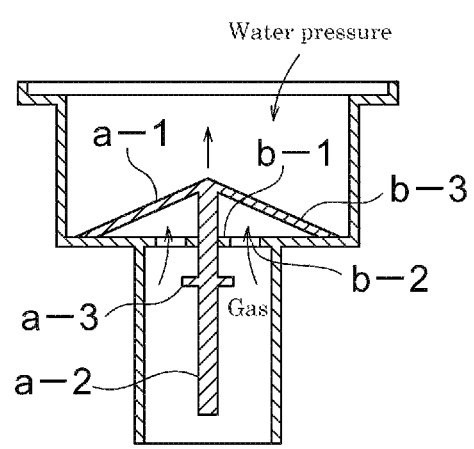
FIG. 1B is a cross-sectional view illustrating the gas/liquid separating section according to one embodiment of the present invention.

FIG. 1 illustrates an example of the gas/liquid separating section employing such an open-close type valve. In this case, the gas/liquid separating section is comprised of an open-close type valve (a) and a recessed component (b) made of plastic with which the valve is combined. The open-close type valve is configured such that one axial part (a-2) extends from a lampshade-like head part (a-1) while an annular flange (a-3) is shaped at a midway along the axial part so as to surround it. In addition, the recessed component is configured such that the base plate thereof is formed therein with a center hole (b-1) and three holes (b-2) each spread out in a fan-like form are opened to surround the center hole (b-1), while an edge (b-3) remains as a peripheral portion of the base plate to be engaged with the head part of the valve. This base plate has an area with such an extent that the head part (a-1) of the valve is just stored, and when the head part (a-1) of the valve has been stored, the axial part (a-2) of the valve is allowed to pass through the above-described center hole (b-1) opened at the center portion, whereas the annular flange (a-3) surrounding the axial part is not allowed to easily pass therethrough due to its size. However, if the axial part (a-2) having passed through the center hole (b-1) opened at the center portion of the base plate of the recessed component is pulled down from below, then the annular flange (a-3) surrounding the axial part of the valve passes through the hole (b-1) of the base plate while being deformed, thereby to allow for combining the valve (a) and the recessed component (b).

As the gas pressure of hydrogen gas generated in the hydrogen bubble forming implement increases, the hydrogen gas is exhausted while the head part of the open-close type valve having been located at the base plate of the recessed component is pressed and opened, but the annular flange surrounding the axial part is engaged with the center hole opened at the center portion of the base plate of the recessed component, and the open-close valve is thus prevented from dropping off from the recessed component even due to the hydrogen gas pressure during the exhaust.

In addition to this, by further decreasing the amount of the generating-purpose water to be introduced into the hydrogen bubble forming implement, the generating-purpose water is prevented from flowing out into the living organism applicable fluid even during the exhaust of hydrogen gas from the valve.

With respect to a target of the usage of the generating-purpose water, when the hydrogen generating system is removed (in the case where the hydrogen generating system is covered by a cover material, removed with the cover material) after the generating-purpose water has been introduced into the hydrogen bubble forming implement storing the hydrogen generating system, it is desirable that the amount of the generating-purpose water remaining in the hydrogen bubble forming implement is 10 cc or less, preferably 5 cc or less, more preferably 3 cc or less, and most preferably 1 cc or less.

Moreover, for the sake of avoiding the flowing out of such excess generating-purpose water, it is desirable that substances or materials having water absorbability, such as absorbent beads, ion-exchange resin (dry ion-exchange resin is further preferable because of higher water absorbability as will be described later), absorbent paper, hyaluronic acid, and polyacrylic acid, are involved in the hydrogen bubble forming implement or in the cover material as will be described later, etc.

Note that a part or whole of the hydrogen bubble forming implement may be configured of such a gas/liquid separating section. It is desirable that materials provided with the hydrogen bubble forming implement for parts other than the gas/liquid separating section are those, such as acrylic resin and other synthetic resins, which are scarcely permeated with water and hard to be corroded by water.

Another embodiment of the present invention involves, for example, providing the gas/liquid separating section with a gas-permeable film which allows water to flow into the hydrogen bubble forming implement while preventing water to flow out from the hydrogen bubble forming implement, i.e. controls inflow and outflow of water irreversibly. By contacting the equipment for producing living organism applicable hydrogen-contained fluid having such a gas/liquid separating section with the living organism applicable fluid, a part of the living organism applicable fluid flows into the hydrogen bubble forming implement via the gas/liquid separating section. The living organism applicable fluid having flowed thereto reacts as the generating-purpose water with the hydrogen generating system in the hydrogen bubble forming implement thereby to generate hydrogen gas. This causes the generated hydrogen gas to be released into the living organism applicable fluid while avoiding the generating-purpose water to flow out into the living organism applicable fluid owing to the block by the gas-permeable film.

The hydrogen generating system in the present invention may contain agents, such as sequestering agent and pH adjuster, which facilitate the hydrogen generating reaction, in addition to the hydrogen generating agent.

Such a sequestering agent contains one or more substances for generating one or more substances which are absolutely undissolved or scarcely dissolved in water and has a property for adsorbing metal ions in the hydrogen bubble forming implement or in the cover material. Insoluble or poorly-soluble metal sequestering agents such as cation exchange resin are preferably used. Among them, hydrogen ion type cation exchange resins are more preferred because of having an additional function as pH adjuster, wherein the hydrogen ion type cation exchange resins include an acidic cation exchange resin having sulfonic acid group as exchange group and an acidic cation exchange resin having carboxylic acid group as exchange group, both of which adsorb metal ions and release hydrogen ions ($H^+$).

Examples of the pH adjuster in the present invention include substances having properties for inhibiting (neutralizing or preventing the generation of) hydroxide ions ($OH^-$) by supplying hydrogen ions ($H^+$), such as citric acid, adipic acid, malic acid, acetic acid, succinic acid, gluconic acid, lactic acid, phosphoric acid, hydrochloric acid, sulfuric acid, and other acids, and further include substances for removing hydroxide ions by being subjected to hydrolysis to form insoluble hydroxide. In addition to acid, alkaline agent such as calcium hydroxide, calcium oxide or anion-exchange resin may also be used when amphoteric metal such as aluminum or zinc is used as the hydrogen generating agent. Among them, it is preferred to use alkaline agent, such as calcium hydroxide (hydrated lime), calcined lime (calcium oxide), burnt calcium, magnesium oxide, magnesium hydroxide, or anion-exchange resin, which is a food additive. A hydrogen generating reaction accelerator that reacts with metal, such as aluminum, which has higher ionization tendency than hydrogen and which is a food additive, to generate poorly-soluble products is suitable for objects of the present invention of substantially not changing properties of the living organism applicable fluid, because the hydrogen generating reaction accelerator suppresses metal ions of the metal from re-dissolving after the hydrogen generating reaction.

In addition, it is preferred that, in order to suppress time degradation of the hydrogen generating agent, the hydration number and the water content ratio of the pH adjuster, such as an appropriate acid or alkaline agent, contained in the hydrogen generating system are lower. More specifically, with respect to the hydration number, it is desirable to be trihydrate or lower, preferably dihydrate or lower, more preferably monohydrate or lower, and most preferably non-hydrate or anhydride. It is also desirable that the water content ratio is 40 weight % or less, preferably 30 weight % or less, more preferably 20 weight % or less, and most preferably 15 weight % or less.

Concepts of the living organism applicable high concentration hydrogen-contained fluid in the present invention include a living organism applicable hydrogen-contained fluid of which the dissolved hydrogen concentration in the fluid is 0.01 ppm or more, preferably 0.1 ppm or more, and more preferably 1.0 ppm or more. Concepts of the living organism applicable supersaturated hydrogen-contained fluid in the present invention involve a situation where the dissolved hydrogen concentration is higher than or equal to the degree of solubility at ordinary temperatures and pressures, and include a living organism applicable high concentration hydrogen-contained fluid of 1.6 ppm or more, 2.0 ppm or more, 3.0 ppm or more, 4.0 ppm or more, 5.0 ppm or more, 6.0 ppm or more, 7.0 ppm or more, 8.0 ppm or more, 9.0 ppm or more, and 10.0 ppm or more.

Note that the selective hydrogen adding equipment for living organism applicable fluid according to the present invention, which is configured by accommodating the hydrogen generating system into the hydrogen bubble forming implement, may be disposed within a container for storing the living organism applicable fluid so as to be, such as, in the living organism applicable fluid, in the air space of the container, or in the outer space of the container. Note also that the container is preferred to be a closed container.

When using a closed container as the container, the hydrogen gas generated in the hydrogen bubble forming implement by the reaction between the hydrogen generating system and the generating-purpose water is released via the gas/liquid separating section of the hydrogen bubble forming implement into the closed container storing the living organism applicable fluid and forms a hydrogen gas phase of high pressure and high concentration. Note that the applicant(s) have found out that, even when the selective hydrogen adding equipment for living organism applicable fluid according to the present invention is disposed in the living organism applicable fluid, most of the generated hydrogen molecules first transfer toward the air space of the closed container without dissolving into the living organism applicable fluid.

Further to say, the applicant(s) have found out that, when the hydrogen generating agent is disposed in the living organism applicable fluid after being stored in the hydrogen bubble forming implement, the amount of hydrogen dissolving into the living organism applicable fluid immediately after being put into the fluid is further less than the case where the hydrogen generating agent is put in a bared state into the living organism applicable fluid without being stored in the hydrogen bubble forming implement.

That is, hydrogen molecules generated from the hydrogen generating agent not stored in the hydrogen bubble forming implement come to form clusters or microscopic bubbles while directly dissolving into the living organism applicable fluid, whereas, when hydrogen molecules are released into the living organism applicable fluid via the gas/liquid separating section of the hydrogen bubble forming implement, the hydrogen bubble forming implement acts as a kind of stopper for the hydrogen gas, thereby resulting in that the hydrogen molecules once gather together with an appropriate amount at the vicinity of the inner wall of the gas/liquid separating section and are thereafter released as hydrogen gas bubbles from the gas/liquid separating section. In other words, when released into the living organism applicable fluid, the hydrogen molecules are released as hydrogen gas bubbles already having certain dimensions.

This is visually observed. For example, if the selective hydrogen adding equipment for living organism applicable fluid according to the present invention is disposed in the closed container storing the living organism applicable fluid and the container is left for a while in a laid form, then the hydrogen gas generated in the hydrogen bubble forming implement releases intermittently hydrogen bubbles from the gas/liquid separating section while causing the volume of the hydrogen gas phase to be progressively increased. In other words, the released hydrogen gas is of large bubble size, therefore moving upward in water to rapidly transfer into the gas phase in the closed container.

In general, among ones of ordinary skill in the art of producing not only hydrogen-contained solution but other gas-contained solution with expectation of some form of industrial use, it has been considered that the important thing for producing a high-concentration gas solution is to make the bubble size of the gas be microscopic as much as possible thereby decreasing the rising velocity of the bubbles toward the gas phase. At the time of the present application, it still remains to be recognized as one of primary technical issues in the art to make various industrial gasses including hydrogen, oxygen or ozone be nano-bubbles.

Meanwhile, the inventors have found out that, in the case where consumers attempt to obtain a living organism applicable high concentration hydrogen-contained fluid at various locations, such as home, workplace, street, and storefront, it is desirable to form first the hydrogen gas phase in the closed container using hydrogen gas of relatively large bubble size and increase the internal pressure in the container, thereafter, if necessary, appropriately shaking the closed container to collect the hydrogen gas from the gas phase, than directly dissolving hydrogen molecules into the living organism applicable fluid in the closed container which stores the living organism applicable fluid including drinking water and beverages, such as tea and coffee. Therefore, it is desirable that the gas-permeable film or the valve to be used for the gas/liquid separating section is such that, when the equipment according to the present invention having the gas/liquid separating section is disposed in clarified water, the average bubble diameter of hydrogen gas bubbles generated during initial 10 minutes is 0.1 mm or more, preferably 0.3 mm or more, more preferably 0.5 mm or more, and most preferably 1.0 mm or more, when measured by using dynamic light scattering method or other appropriate method.

According to experiments performed by the inventors, in spite of the fact that the dissolved hydrogen concentration in the living organism applicable fluid increases up to approximately 0.7 ppm after a lapse of 10 minutes from a situation where metal magnesium as the hydrogen generating agent has been disposed in the living organism applicable fluid in the closed container without being stored in the hydrogen bubble forming implement, subsequent shaking of the closed container merely increases the dissolved hydrogen concentration up to approximately 0.9 ppm (approximately 1.3 times). In contrast, the dissolved hydrogen concentration in the living organism applicable fluid slightly increases up to approximately 0.2 ppm after a lapse of 10 minutes from a situation where the same amount of metal magnesium as the hydrogen generating agent has been disposed in the living organism applicable fluid in the closed container with being stored in the hydrogen bubble forming implement, whereas subsequent shaking of the closed container drastically increases the dissolved hydrogen concentration up to approximately 3.0 ppm (approximately 15 times).

Thus, it is desirable to accommodate in the closed container the hydrogen adding equipment for living organism applicable fluid according to the present invention, which is configured by storing the hydrogen generating system in the hydrogen bubble forming implement, and to appropriately shake the closed container, for the purpose of increasing the dissolved hydrogen concentration in the living organism applicable hydrogen-contained fluid.

In this case, the closed container in the present invention is intended to include a container which is devised not to expose the contents in the container to the air. Examples of the closed container include containers with lids, such as PET bottles and aluminum bottles with caps. It is desirable that the container has a portable form and volume in order for a person to easily shake it in his/her hand. It is also desirable that the container is of 2 L or less, preferably 1 L or less, and most preferably 0.5 L or less, but not limited thereto.

Preferred materials for the closed container are to have low hydrogen permeability. As the hydrogen permeability is lower, the generated hydrogen is hard to escape from the container system.

The hydrogen permeability of the closed container in the present invention is measured as follows. That is, with reference to the method described in Patent Application No. 2009-221567 or the like, hydrogen dissolved water is prepared to stably keep approximately the saturated concentration (1.6 ppm at 20 degrees C. and 1 atm) with the volume of 20 times of the inner volume of a closed container as an object to be measured, and the closed container is then immersed during 5 hours in the hydrogen dissolved water after being fully filled with clarified water (charcoal-treated water, such as Fujisawa city tap water treated to pass through a charcoal column).

Thereafter, the dissolved hydrogen concentration in the clarified water is measured, wherein the container of lower hydrogen permeability in the present invention involves a closed container with dissolved hydrogen concentration of 1,000 ppb or lower, preferably 500 ppb or lower, more preferably 100 ppb or lower, and most preferably 10 ppb or lower.

It is desirable that the closed container has a pressure-proof property capable of resisting the increasing of the inner pressure due to the generation of hydrogen. Specifically, it is desirable to be a pressure-proof container capable of resisting the inner pressure of 0.11 MPa as absolute pressure, preferably 0.4 MPa, more preferably 0.5 MPa, and most preferably 0.8 MPa. A PET bottle for carbonated drink or any appropriate bottle may be preferably used. It is also desirable that the closed container comprises at the mouth thereof a mechanism for releasing the pressure (vent slot) midway through opening the cap for the purpose of safety opening.

The shaking in the present invention is to give a physical impact or shock to the closed container thereby replacing the dissolved gas such as dissolved oxygen in the living organism applicable fluid with hydrogen gas while contacting the living organism applicable fluid and the gas-phase hydrogen with each other in the closed container. The shaking in the present invention involves natural shaking using hand or hands as well as artificial shaking using a machine. Examples of such artificial shaking include shaking by using a shaking machine, an agitator, an ultrasonic generator, and other appropriate apparatuses.

Moreover, in order for hydrogen gas to be further accumulated in the gas phase in the closed container, it is desirable to start the shaking after 1 minute has elapsed, preferably 2 minutes, more preferably 4 minutes, furthermore preferably 8 minutes, and most preferably 10 minutes, from the time when the selective hydrogen adding equipment for living organism applicable fluid according to the present invention was disposed in the closed container.

Note that an exemplary case of typical and natural shaking in the present invention is as follows. That is, the shaking is performed by a Japanese man of 30's having an average physical size, who holds the middle portion of the closed container by his dominant hand and moves only the wrist to shake it such that the cap forms into an arch above the wrist with a pace of 2 strokes per second, total 120 strokes.

Further, in order to facilitate the dissolution of the high-pressure and high-concentration hydrogen gas into the living organism applicable fluid, it is desirable that the time period for the shaking is 5 seconds or longer for the natural shaking, preferably 10 seconds or longer, more preferably 15 seconds or longer, and still preferably 30 seconds or longer.

Moreover, it is preferred that the shaking is such that, when performing the shaking after disposing the selective hydrogen adding equipment for living organism applicable fluid according to the present invention in the living organism applicable fluid, the dissolved hydrogen concentration in the living organism applicable fluid is enhanced twice or higher of the dissolved hydrogen concentration before the shaking, preferably 3 times or higher, more preferably 4 times or higher, 5 times or higher, 6 times or higher, 7 times or higher, 8 times or higher and 9 times or higher in this order, and further preferably 10 times or higher.

Furthermore, it is preferred that the inner pressure in the closed container before the shaking is higher than or equal to the atmosphere pressure in order to obtain higher concentration living organism applicable hydrogen-contained fluid, such as supersaturated living organism applicable hydrogen-contained fluid with 1.6 ppm or higher. The solubility of hydrogen molecules to the living organism applicable fluid increases as the inner pressure loaded by the generated hydrogen molecules to the closed container increases, and exceeds the solubility at the normal temperature and pressure in due time. The reason why the closed container storing the hydrogen generating system is left for a while for example in the examples as will be described later is to pressurize the closed container from the inside by the generated hydrogen gas, and also to allow for appropriately shaking the closed container under the increased pressure thereby further facilitating the dissolution of the hydrogen molecules to the living organism applicable hydrogen-contained fluid.

Note that the conditions of not substantially changing the constituents of the living organism applicable fluid in the present invention include, such as, but not limited to, satisfying at least either one of not changing the total hardness, not changing the metal ion concentration related to the metal used as the hydrogen generating agent, or not changing the pH.

Here, the conditions of not changing the total hardness of the living organism applicable fluid include the following cases, but are not limited thereto.

Such cases include a case where the total hardness (Ca hardness+Mg hardness) in the living organism applicable hydrogen-contained fluid of which the raw water is a certain living organism applicable fluid is within an allowable range, such as, from (total hardness of the raw water minus 25 ppm) to (total hardness of the raw water plus 25 ppm), preferably from (total hardness of the raw water minus 15 ppm) to (total hardness of the raw water plus 15 ppm), and more preferably from (total hardness of the raw water minus 10 ppm) to (total hardness of the raw water plus 10 ppm).

Alternatively, such cases may include a case where a PET bottle for carbonated drink (about 530 cc volume when filled with full water to the mouth) is substantially filled with 515 cc of living organism applicable fluid as being clarified water obtained by dechlorination treating for tap water and having total hardness (Ca hardness+Mg hardness) of approximately 55 to 65 ppm (clarified water such as obtained by treating Fujisawa city tap water to pass through a charcoal column), the nondestructive producing equipment for high-concentration hydrogen solution according to the present invention is disposed in the living organism applicable fluid, the bottle is left to be laid flat during 10 minutes, and the total hardness of the fluid after performing typical and natural shaking (holding the middle portion of the PET bottle by one's dominant hand and moving only the wrist such that the cap forms into an arch above the wrist with a pace of 2 strokes per second, total 120 strokes) for the fluid is within an allowable range, such as, from (total hardness of the raw water minus 25 ppm) to (total hardness of the raw water plus 25 ppm), preferably from (total hardness of the raw water minus 15 ppm) to (total hardness of the raw water plus 15 ppm), and most preferably from (total hardness of the raw water minus 10 ppm) to (total hardness of the raw water plus 10 ppm).

Here, the conditions of not changing the metal ion concentration related to the metal used as the hydrogen generating agent include the following cases, but are not limited thereto.

Such cases include a case where the metal ion concentration (aluminum ion concentration when the equipment according to the present invention uses aluminum as the hydrogen generating agent, for example) in the living organism applicable hydrogen-contained fluid of which the raw water is a certain living organism applicable fluid is within an allowable range, such as, from (metal ion concentration of the raw water minus 15 ppm) to (metal ion concentration of the raw water plus 15 ppm), preferably from (metal ion concentration of the raw water minus 10 ppm) to (metal ion concentration of the raw water plus 10 ppm), more preferably from (metal ion concentration of the raw water minus 5 ppm) to (metal ion concentration of the raw water plus 5 ppm), furthermore preferably from (metal ion concentration of the raw water minus 3 ppm) to (metal ion concentration of the raw water plus 3 ppm), and most preferably from (metal ion concentration of the raw water minus 1 ppm) to (metal ion concentration of the raw water plus 1 ppm).

Alternatively, such cases may include a case where a PET bottle for carbonated drink (about 530 cc volume when filled with full water to the mouth) is substantially filled with 515 cc of living organism applicable fluid as being clarified water obtained by dechlorination treating for tap water (clarified water such as obtained by treating Fujisawa city tap water to pass through a charcoal column), the producing equipment for living organism applicable hydrogen-contained fluid according to the present invention is disposed in the living organism applicable fluid, the bottle is left to be laid flat during 10 minutes, and immediately after performing typical and natural shaking (holding the middle portion of the PET bottle by one's dominant hand and moving only the wrist such that the cap forms into an arch above the wrist with a pace of 2 strokes per second, total 120 strokes) for the fluid, the metal ion concentration in the fluid related to the metal used as the hydrogen generating agent in the producing equipment (aluminum ion concentration when the equipment according to the present invention uses aluminum as the hydrogen generating agent, for example) is within an allowable range, such as, from (metal ion concentration of the raw water minus 15 ppm) to (metal ion concentration of the raw water plus 15 ppm), preferably from (metal ion concentration of the raw water minus 10 ppm) to (metal ion concentration of the raw water plus 10 ppm), more preferably from (metal ion concentration of the raw water minus 5 ppm) to (metal ion concentration of the raw water plus 5 ppm), furthermore preferably from (metal ion concentration of the raw water minus 3 ppm) to (metal ion concentration of the raw water plus 3 ppm), and most preferably from (metal ion concentration of the raw water minus 1 ppm) to (metal ion concentration of the raw water plus 1 ppm).

Here, the conditions of not changing the pH include the following cases, but are not limited thereto.

Such cases include a case where the pH in the living organism applicable hydrogen-contained fluid of which the raw water is a certain living organism applicable fluid is within an allowable range, such as, from (pH of the raw water minus 3.0) to (pH of the raw water plus 3.0), preferably from (pH of the raw water minus 2.0) to (pH of the raw water plus 2.0), more preferably from (pH of the raw water minus 1.0) to (pH of the raw water plus 1.0), and most preferably from (pH of the raw water minus 0.5) to (pH of the raw water plus 0.5).

Alternatively, such cases may include a case where a PET bottle for carbonated drink (about 530 cc volume when filled with full water to the mouth) is substantially filled with 515 cc of living organism applicable fluid as being clarified water obtained by dechlorination treating for tap water and having pH of approximately 7.0 to 7.8 (clarified water such as obtained by treating Fujisawa city tap water to pass through a charcoal column), the producing equipment for living organism applicable hydrogen-contained fluid according to the present invention is disposed in the living organism applicable fluid, the bottle is left to be laid flat during 10 minutes, and immediately after performing typical and natural shaking (holding the middle portion of the PET bottle by one's dominant hand and moving only the wrist such that the cap forms into an arch above the wrist with a pace of 2 strokes per second, total 120 strokes) for the fluid, the pH of the fluid is within an allowable range, such as, from (pH of the raw water minus 3.0) to (pH of the raw water plus 3.0), preferably from (pH of the raw water minus 2.0) to (pH of the raw water plus 2.0), more preferably from (pH of the raw water minus 1.0) to (pH of the raw water plus 1.0), and most preferably from (pH of the raw water minus 0.5) to (pH of the raw water plus 0.5).

EXAMPLES

Hereinafter, examples of the present invention will be described. Note that, when there is no particular explanation in the present application, various gauges used for measuring various physicality values are as follows: pH meter (including temperature indicator) manufactured by Horiba, Ltd. (main body type: D-13, probe type: 9620-10D); and DH meter (dissolved hydrogen meter) manufactured by DKK-Toa Corporation (main body type: DHDI-1, electrode (probe) type: HE-5321, transponder type: DHM-F2).

Calcium hardness and magnesium hardness were measured by the calmagite colorimetric method using water quality analyzer DR/4000 (manufactured by HACH Company).

Aluminum ion concentration was measured by the aluminon method using the same water quality analyzer.

Figure 2:
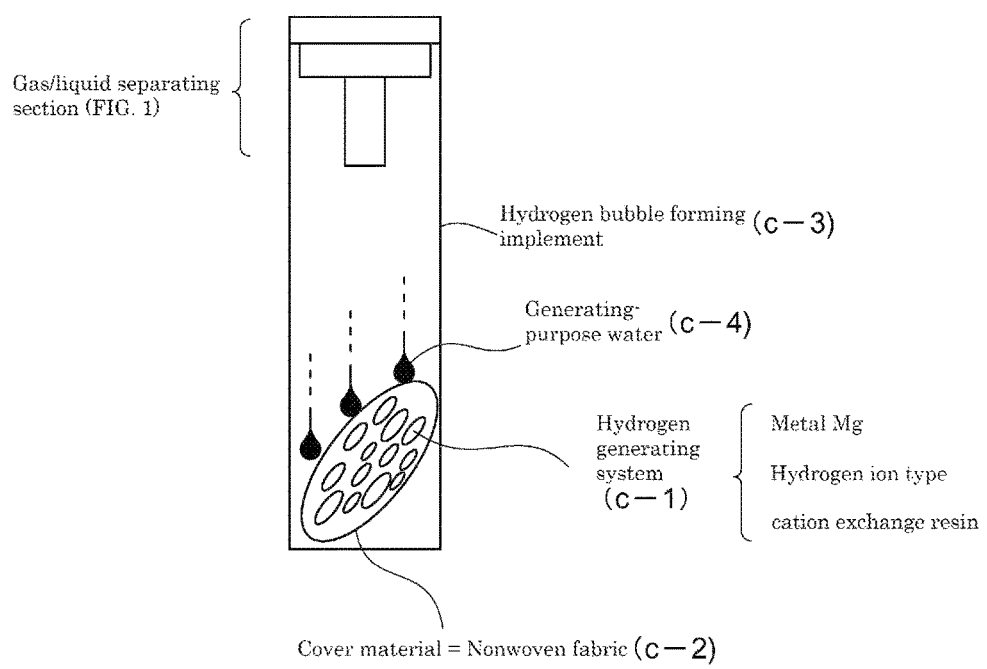
FIG. 2 is a front elevational view illustrating a selective hydrogen adding equipment in which the gas/liquid separating section shown in FIGS. 1A and 1B is attached to a hydrogen bubble forming implement.

Example 1 (Illustrated as FIG. 2)

A hydrogen generating system (c-1) containing 300 mg of metal magnesium (MG100: Kanto Metal Corporation) as the hydrogen generating agent and further containing 1,500 mg of hydrogen ion type cation exchange resin (obtained by thermally-drying "DIAION Ion Exchange Resin SK1BH: Mitsubishi Chemical Corporation", a commercially available strongly acidic ion exchange resin H-type product) was enclosed and heat sealed in a cover material (Precisé Regular C5160: Asahi Kasei Corporation) (c-2), and then stored in an acrylic resin tubular hydrogen bubble forming implement (c-3) with that cover material. The selective hydrogen adding equipment for living organism applicable fluid according to the present invention was obtained by dropping generating-purpose water (c-4) into the hydrogen bubble forming implement with such an extent of wetting the cover material, and closing the opening of the hydrogen bubble forming implement with the gas/liquid separating section (FIG. 1).

Subsequently, a PET bottle for carbonated drink (about 530 cc volume when filled with full water to the mouth) was substantially filled with about 515 cc of clarified water (charcoal-treated water obtained by treating Fujisawa city tap water to pass through a charcoal column), and the selective hydrogen adding equipment for living organism applicable fluid was then disposed into the clarified water in the PET bottle.

Thereafter, the bottle was left to be laid flat during 10 minutes, and one of the present inventors (Japanese man of 30's having an average physical size) then held the middle portion of the PET bottle by his dominant hand and moved only the wrist to shake it such that the cap was forming into an arch above the wrist with a pace of 2 strokes per second, total 120 strokes (total 60 seconds).

Measurements were done for pH, dissolved hydrogen concentration, calcium (Ca) hardness, and magnesium (Mg) hardness of contained fluid before and after shaking.

Figure 3:
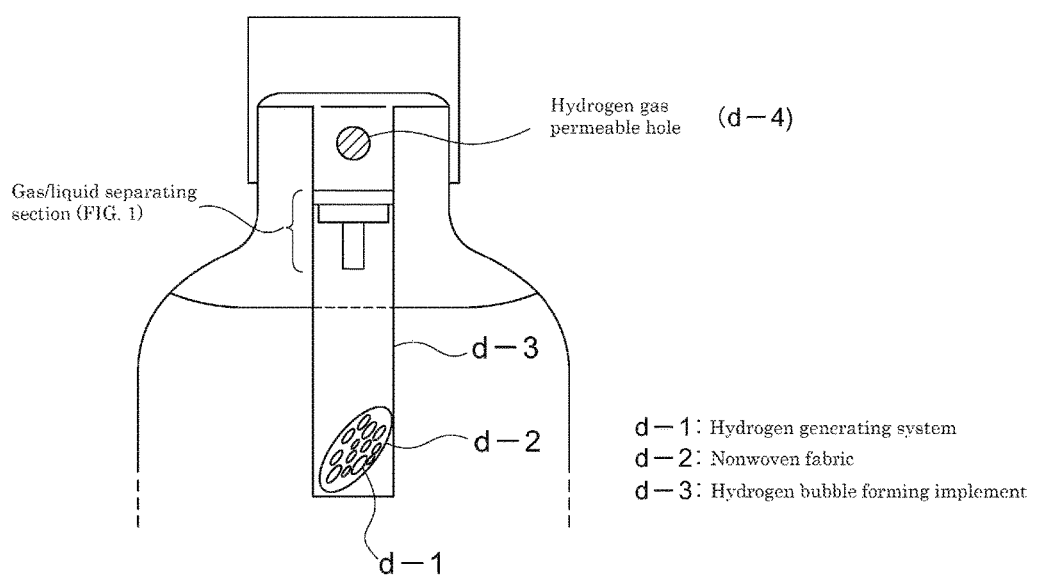
FIG. 3 is a front elevational view illustrating another example of selective hydrogen adding equipment in which the gas/liquid separating section shown in FIGS. 1A and 1B is attached to a hydrogen bubble forming implement.

Example 2 (Illustrated as FIG. 3)

A hydrogen generating system (d-1) containing 300 mg of metal magnesium (MG100: Kanto Metal Corporation) as the hydrogen generating agent and further containing 1,500 mg of hydrogen ion type cation exchange resin (obtained by thermally-drying "DIAION Ion Exchange Resin SK1BH: Mitsubishi Chemical Corporation", a commercially available strongly acidic ion exchange resin H-type product) was enclosed and heat sealed in a cover material (Precisé Regular C5160: Asahi Kasei Corporation) (d-2), and then stored in an acrylic resin tubular hydrogen bubble forming implement (d-3) with that cover material. The selective hydrogen adding equipment for living organism applicable fluid according to the present invention was obtained by dropping water into the hydrogen bubble forming implement with such an extent of wetting the cover material, inserting the gas/liquid separating section described with reference to FIG. 1 to be disposed into the tubular hydrogen bubble forming implement so as just not to leave a space at the middle portion, and opening one or more hydrogen gas permeable holes (d-4) at a part of the outer wall of the hydrogen bubble forming implement.

Subsequently, a PET bottle for carbonated drink (about 530 cc volume when filled with full water to the mouth) was substantially filled with about 515 cc of clarified water (charcoal-treated water obtained by treating Fujisawa city tap water to pass through a charcoal column), and the fringe of the hydrogen bubble forming implement was then caused to engage with the PET bottle mouth portion while the equipment was inserted into the mouth portion and the cap was closed so as not to immerse the equipment in the water. At that time, the hydrogen gas permeable holes were positioned above the water level of the clarified water.

Thereafter, the bottle was left during 10 minutes, and one of the present inventors (Japanese man of 30's having an average physical size) then held the middle portion of the PET bottle by his dominant hand and moved only the wrist to shake it such that the cap was forming into an arch above the wrist with a pace of 2 strokes per second, total 120 strokes (total 60 seconds).

Measurements were done for pH, dissolved hydrogen concentration, calcium (Ca) hardness, and magnesium (Mg) hardness of contained fluid before and after shaking.

Example 3

A hydrogen generating system containing 300 mg of metal magnesium (MG100: Kanto Metal Corporation) as the hydrogen generating agent and further containing 900 mg of malic acid (DL-malic acid: FUSO CHEMICAL CO., LTD.) was enclosed with water absorbent paper and heat sealed in a cover material (Precisé Regular C5160: Asahi Kasei Corporation), and then stored in an acrylic resin tubular hydrogen bubble forming implement with that cover material. The selective hydrogen adding equipment for living organism applicable fluid according to the present invention was obtained by dropping water into the hydrogen bubble forming implement with such an extent of wetting the cover material, inserting a stopper made of water absorbent paper and in turn the gas/liquid separating section described with reference to FIG. 1 to be disposed into the tubular hydrogen bubble forming implement so as just not to leave a space at the middle portion, and opening one or more hydrogen gas permeable holes at a part of the outer wall of the hydrogen bubble forming implement.

Subsequently, a PET bottle for carbonated drink (about 530 cc volume when filled with full water to the mouth) was substantially filled with about 515 cc of clarified water (charcoal-treated water obtained by treating Fujisawa city tap water to pass through a charcoal column), and the fringe of the hydrogen bubble forming implement was then caused to engage with the PET bottle mouth portion while the equipment was inserted into the mouth portion and the cap was closed so as not to immerse the equipment in the water. At that time, the hydrogen gas permeable holes were positioned above the water level of the clarified water.

Thereafter, the bottle was left during 10 minutes, and one of the present inventors (Japanese man of 30's having an average physical size) then held the middle portion of the PET bottle by his dominant hand and moved only the wrist to shake it such that the cap was forming into an arch above the wrist with a pace of 2 strokes per second, total 120 strokes (total 60 seconds).

Measurements were done for pH, dissolved hydrogen concentration, calcium (Ca) hardness, and magnesium (Mg) hardness of contained fluid before and after shaking.

Comparative Example 1

A hydrogen generating system was prepared to contain 300 mg of metal magnesium as the hydrogen generating agent and further contain 1,500 mg of hydrogen ion type cation exchange resin (obtained by thermally-drying "DIAION Ion Exchange Resin SK1BH: Mitsubishi Chemical Corporation", a commercially available strongly acidic ion exchange resin H-type product).

A PET bottle for carbonated drink (about 530 cc volume when filled with full water to the mouth) was substantially filled with about 515 cc of clarified water (charcoal-treated water obtained by treating Fujisawa city tap water to pass through a charcoal column), and the hydrogen generating system was then put directly into the clarified water in the PET bottle.

Thereafter, the bottle was left during 10 minutes, and one of the present inventors (Japanese man of 30's having an average physical size) then held the middle portion of the PET bottle by his dominant hand and moved only the wrist to shake it such that the cap was forming into an arch above the wrist with a pace of 2 strokes per second, total 120 strokes (total 60 seconds).

Measurements were done for pH, dissolved hydrogen concentration, calcium (Ca) hardness, and magnesium (Mg) hardness of contained fluid before and after shaking.

Reference Example 1

Measurements were done for pH, dissolved hydrogen concentration, calcium (Ca) hardness, and magnesium (Mg) hardness of the clarified water used in the Examples and the Comparative Example.

Results are shown as follows in Table 1.

TABLE 1

|  | Mg (mg) | SK1BH or Malic Acid (mg) | Mg:SK1BH or Malic Asid | Generating-purpose water amount (cc) | Hydrogen bubble forming implement |
|---|---|---|---|---|---|
| Example 1 | 300 | 1500 | 1:5 | 2 | Present |
| Example 2 | 300 | 1500 | 1:5 | 2 | Present |
| Example 3 | 300 | 900 | 1:3 | 1 | Present |
| Comparative Example 1 | 300 | 1500 | 1:5 |  | Absent |
| Reference Example 1 |  |  |  |  |  |

|  | Bottle | pH | Ca hardness (ppm) | Mg hardness (ppm) | DH (ppm) |
|---|---|---|---|---|---|
| Example 1 | Laid | Before: 7.38 | Before: 40 | Before: 20 | Before: 0.24 |
|  |  | After: 7.33 | After: 41 | After: 18 | After: 3.0 |
| Example 2 | Stand | Before: 7.33 | Before: 41 | Before: 18 | Before: 0.06 |
|  |  | After: 7.34 | After: 40 | After: 19 | After: 2.90 |
| Example 3 | Stand | Before: 7.34 | Before: 41 | Before: 22 | Before: 0.06 |
|  |  | After: 7.34 | After: 42 | After: 21 | After: 1.5 |
| Comparative Example 1 | Stand | Before: 10.54 | Before: 39 | Before: 75 | Before: 1.04 |
|  |  | After: 10.61 | After: 38 | After: 81 | After: 1.15 |
| Reference Example 1 |  | 7.32 | 41.00 | 20.00 | 0.00 |

SK1BH = Strongly acidic ion exchange resin H-type product, Grain size: about 425 μm to 1180 μm
Before and After mean before and after shaking
Left during 10 minutes then shaking 60 seconds

Figure 4:
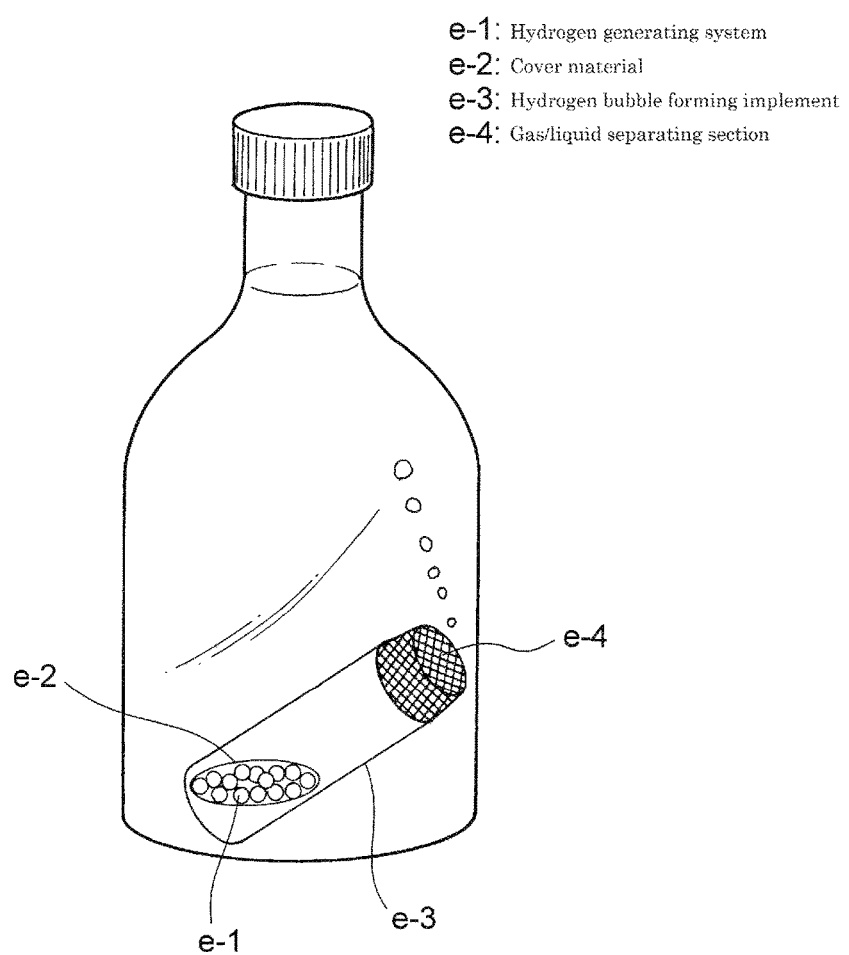
FIG. 4 is a front elevational view illustrating another example of selective hydrogen adding equipment in which the gas/liquid separating section as a gas-permeable film is attached to a hydrogen bubble forming implement.

Example 4 (Illustrated as FIG. 4)

Hydrogen generating system (e-1) was obtained by mixing metal aluminum grains (grain diameter: 53 to 150 μm, 80% up) (Wako Pure Chemical Industries, Ltd., hereinafter the same applies) and calcium hydroxide (Wako Pure Chemical Industries, Ltd., hereinafter the same applies). The obtained hydrogen generating system contained metal aluminum grains 85 weight % and calcium hydroxide 15 weight %.

The hydrogen generating system 0.8 g was enclosed and heat sealed in a cover material (Precisé Regular C5160: Asahi Kasei Corporation) (e-2), and then stored in an acrylic resin tubular hydrogen bubble forming implement (e-3) with that cover material and 7.3 g of stainless weight. The selective hydrogen adding equipment for living organism applicable fluid according to the present invention was obtained by dropping 0.3 cc of water (generating-purpose water) into the hydrogen bubble forming implement, and closing the opening of the hydrogen bubble forming implement with a gas-permeable film (Monotoran Film, Type No.: FP10-01105-100, Nac Corporation) as the gas/liquid separating section (e-4).

Subsequently, a PET bottle for carbonated drink (about 530 cc volume when filled with full water to the mouth) was substantially filled with about 515 cc of clarified water (charcoal-treated water obtained by treating Fujisawa city tap water to pass through a charcoal column), and the selective hydrogen adding equipment for living organism applicable fluid was then disposed into the clarified water in the PET bottle. Three sets of the same were prepared.

Respective bottles were closed with their caps and left during 3 minutes, 5 minutes, and 10 minutes.

Thereafter, one of the present inventors (Japanese man of 30's having an average physical size) held the middle portion of the PET bottle by his dominant hand and moved only the wrist to shake it such that the cap was forming into an arch above the wrist with a pace of 2 strokes per second, total 120 strokes (total 60 seconds).

Then, measurements were done for pH, dissolved hydrogen concentration (DH), and aluminum (Al) ion concentration of each content fluid.

Example 5

The selective hydrogen adding equipment for living organism applicable fluid according to the present invention was obtained without the weight in the selective hydrogen adding equipment for living organism applicable fluid described with reference to Example 4.

Subsequently, a PET bottle for carbonated drink (about 530 cc volume when filled with full water to the mouth) was substantially filled with about 515 cc of clarified water (charcoal-treated water obtained by treating Fujisawa city tap water to pass through a charcoal column), and the equipment was then disposed in the PET bottle. The equipment floated on the clarified water thereby keeping its gas/liquid separating section within the air space in the PET bottle. Three sets of the same were prepared.

Respective bottles were closed with their caps and left during 3 minutes, 5 minutes, and 10 minutes.

Thereafter, one of the present inventors (Japanese man of 30's having an average physical size) held the middle portion of the PET bottle by his dominant hand and moved only the wrist to shake it such that the cap was forming into an arch above the wrist with a pace of 2 strokes per second, total 120 strokes (total 60 seconds).

Then, measurements were done for pH, dissolved hydrogen concentration (DH), and aluminum (Al) ion concentration of each content fluid.

Figure 5:
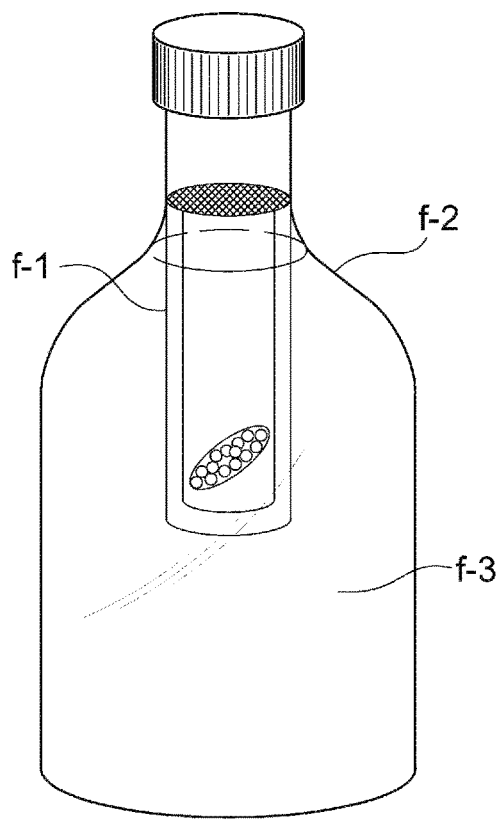
FIG. 5 is a front elevational view illustrating another example of selective hydrogen adding equipment in which an outer shell is attached to the hydrogen bubble forming implement shown in FIG. 4.

Example 6 Illustrated as FIG. 5

The selective hydrogen adding equipment for living organism applicable fluid according to the present invention was obtained with the hydrogen bubble forming implement further stored in an acrylic resin tubular outer shell (f-1) of a size slightly larger than the hydrogen bubble forming implement in the selective hydrogen adding equipment for living organism applicable fluid described with reference to Example 5.

Subsequently, a PET bottle (f-2) for carbonated drink (about 530 cc volume when filled with full water to the mouth) was substantially filled with about 515 cc of clarified water (charcoal-treated water obtained by treating Fujisawa city tap water to pass through a charcoal column) (f-3), and the equipment was then disposed in the PET bottle. The equipment floated on the clarified water thereby keeping its gas/liquid separating section within the air space in the PET bottle. Three sets of the same were prepared.

Respective bottles were closed with their caps and left during 3 minutes, 5 minutes, and 10 minutes.

Thereafter, one of the present inventors (Japanese man of 30's having an average physical size) held the middle portion of the PET bottle by his dominant hand and moved only the wrist to shake it such that the cap was forming into an arch above the wrist with a pace of 2 strokes per second, total 120 strokes (total 60 seconds).

Then, measurements were done for pH, dissolved hydrogen concentration (DH), and aluminum (Al) ion concentration of each content fluid.

Reference Example 2

Measurements were done for pH and aluminum (Al) concentration of the Fujisawa city tap water used for Examples 4 to 6.

Results thereof are shown as follows in Table 2.

TABLE 2

| | Left time | DH (ppm) | pH | Al ion (ppm) | Water temperature (° C.) |
|---|---|---|---|---|---|
| Reference Example 2 | — | — | 7.15 | 0.036 | 22.6 |
| Example 4 | After 3 min. | 0.78 | 7.14 | 0.040 | 23.0 |
| | After 5 min. | 1.11 | 7.13 | 0.037 | 23.5 |
| | After 10 min. | 1.54 | 7.14 | 0.034 | 23.4 |
| Example 5 | After 3 min. | 0.82 | 7.17 | 0.037 | 23.1 |
| | After 5 min. | 1.06 | 7.17 | 0.036 | 23.5 |
| | After 10 min. | 1.48 | 7.17 | 0.036 | 23.5 |
| Example 6 | After 3 min. | 3.20 | 7.17 | 0.034 | 23.0 |
| | After 5 min. | 3.60 | 7.14 | 0.039 | 23.4 |
| | After 10 min. | 3.50 | 7.15 | 0.038 | 23.4 |

Example 7

The hydrogen generating system was obtained by mixing metal aluminum grains and calcium hydroxide powder. The hydrogen generating system was solidified with tableting pressure of 5 kN using a tableting machine (HANDTAB-Jr: Ichihashi Seiki Co., Ltd.). The obtained hydrogen generating system tablets contained metal aluminum grains 85 weight % and calcium hydroxide 15 weight %.

The hydrogen generating system tablets 0.8 g were stored in an acrylic resin tubular hydrogen bubble forming implement (e-3). The selective hydrogen adding equipment for living organism applicable fluid according to the present invention was obtained by dropping 0.3 cc of water (generating-purpose water) into the hydrogen bubble forming implement, and closing the opening of the hydrogen bubble forming implement with a gas-permeable film (Monotoran Film, Type No.: FP10-01105-100, Nac Corporation) as the gas/liquid separating section (e-4).

Subsequently, a PET bottle for carbonated drink (about 530 cc volume when filled with full water to the mouth) was substantially filled with about 515 cc of clarified water (charcoal-treated water obtained by treating Fujisawa city tap water to pass through a charcoal column), and the selective hydrogen adding equipment for living organism applicable fluid was then disposed into the clarified water in the PET bottle. Four sets of the same were prepared.

Respective bottles were closed with their caps and left during 10 minutes, 30 minutes, 60 minutes, and 15 hours.

Thereafter, one of the present inventors (Japanese man of 30's having an average physical size) held the middle portion of the PET bottle by his dominant hand and moved only the wrist to shake it such that the cap was forming into an arch above the wrist with a pace of 2 strokes per second, total 120 strokes (total 60 seconds).

Then, measurements were done for pH and dissolved hydrogen concentration (DH) of each content fluid.

Example 8

The selective hydrogen adding equipment for living organism applicable fluid according to the present invention was similarly obtained except that the tableting pressure was 2.5 kN in the selective hydrogen adding equipment for living organism applicable fluid described with reference to Example 7. Dissolved hydrogen concentration (DH) of each content fluid was measured in a similar procedure as Example 7 (however, only for 10 minutes left, 30 minutes left, and 60 minutes left).

Example 9

The selective hydrogen adding equipment for living organism applicable fluid according to the present invention was similarly obtained except that the tableting pressure was 1.0 kN in the selective hydrogen adding equipment for living organism applicable fluid described with reference to Example 7. Dissolved hydrogen concentration (DH) of each content fluid was measured in a similar procedure as Example 7 (however, only for 10 minutes left, 30 minutes left, and 60 minutes left).

Reference Example 3

Measurements were done for pH and aluminum (Al) concentration of the Fujisawa city tap water used for Example 7.

Reference Example 4

Measurements were done for pH and aluminum (Al) concentration of the Fujisawa city tap water used for Examples 8 to 9.

Results thereof are shown as follows in Table 3.

TABLE 3

|  | Left time | DH (ppm) | pH | Al ion (ppm) |
|---|---|---|---|---|
| Reference Example 3 | — | — | 7.15 | 0.036 |
| Example 7 | After 10 min. | 0.58 | 7.18 | 0.034 |
|  | After 30 min. | 0.72 | 7.16 | 0.035 |
|  | After 1 Hr. | 0.98 | 7.16 | 0.036 |
|  | After 15 Hrs. | 2.20 | 7.25 | 0.038 |
| Reference Example 4 | — | — | 7.25 | 0.028 |
| Example 8 | After 10 min. | 0.68 | — | — |
|  | After 30 min. | 1.36 | — | — |
|  | After 60 min. | 1.50 | | |
| Example 9 | After 10 min. | 1.38 | — | — |
|  | After 30 min. | 1.60 | | |
|  | After 60 min. | 1.80 | | |

Examples pertinent to the above "metal raw material heat generation temperature measurement method" will hereinafter be described.

According to the above "metal raw material heat generation temperature measurement method", the heat generating tendency of each metal raw material was measured. For the metal element of magnesium, the metal raw materials (each 500 mg) used were as follows: Example 10: Mg 20 (0.5 mm: 40% to 60%, 0.3 mm: 20% to 30%, Kanto Metal Corporation), Example 11: Mg grain diameter 1 mm to 2 mm (Chinaroman International Co., Ltd), Example 12: Mg 4 mm pellet (Chinaroman International Co., Ltd), Example 13: tape-like magnesium (Wako Pure Chemical Industries, Ltd.), Comparative Example 2: Mg 100 (0.15 mm or less: 95% or more, Kanto Metal Corporation), and Comparative Example 3: manganese powder (Wako Pure Chemical Industries, Ltd.) (Table 4).

For the metal element of iron, Example 14: reduced iron (Wako Pure Chemical Industries, Ltd.) was used, for the metal element of zinc, Example 15: zinc powder (Wako Pure Chemical Industries, Ltd.) was used, for the metal element of cobalt, Example 16: cobalt powder (Wako Pure Chemical Industries, Ltd.) was used, and for the metal element of aluminum, Example 17: aluminum powder #260 (MINALCO LTD.) was used (Tables 4 and 5).

TABLE 4

| | Each temperature reaching time (seconds) | | | | | |
|---|---|---|---|---|---|---|
| | 50° C. | 60° C. | 70° C. | 80° C. | 90° C. | DH |
| Example 10 | 15 | 19 | 25 | 35 | 49 | 2.05 mg/l |
| Example 11 | 27 | 31 | 35 | 40 | 53 | 1.63 mg/l |
| Example 12 | 70 | 80 | 87 | 95 | 111 | 1.24 mg/l |
| Example 13 | 21 | 23 | 25 | 30 | 35 | 1.82 mg/l |
| Comparative Example 2 | 3 | Not measured | | | | Undetectable |
| Comparative Example 3 | 5 | Not measured | | | | Undetectable |

Tape-like Mg: Total 14 pieces (=0.5 g) were used each cut into the length of 15 to 20 mm

TABLE 5

| | Temperature (° C.) | | | | | | |
|---|---|---|---|---|---|---|---|
| | After 5 min. | After 10 min. | After 15 min. | After 20 min. | After 25 min. | After 30 min. | DH |
| Example 14 | 27.6 | 29.3 | 32.2 | 35.1 | 33.8 | 32.7 | 2.05 mg/l |
| Example 15 | 27.5 | 29.3 | 30.7 | 32.6 | 33.0 | 33.2 | 2.38 mg/l |
| Example 16 | 23.8 | 26.1 | 27.3 | 27.8 | 28.1 | 28.2 | 0.78 mg/l |

| | After 0.5 min. | After 1 min. | After 1.5 min. | After 2 min. | After 2.5 min. | After 3 min. | DH |
|---|---|---|---|---|---|---|---|
| Example 17 | 32.8 | 34.2 | 34.2 | 33.9 | 33.2 | 32.8 | 0.63 mg/l |

As malic acid (500 mg), DL-malic acid (FUSO CHEMICAL CO., LTD.) was used. As aluminum potassium sulfate (500 mg), aluminum potassium sulfate (Wako Pure Chemical Industries, Ltd.) was used. As the generating-purpose water (500 mg), Fujisawa city tap water with the water temperature of 25 to 26 degrees C. was used. As the test tube, Test Tube with 2-position Cap, 17×100 mm, 16.0 mL volume (BM Equipment Co., Ltd.) was used. As the digital thermometer, TANITA TT-508 (TANITA Corporation) was used.

Dissolved hydrogen (DH) concentration achieved by using each metal raw material was measured as the following sequence.

That is, the hydrogen generating system comprised of each metal raw material 500 mg and malic acid 500 mg (or aluminum potassium sulfate if the metal raw material is aluminum) was stored in a polypropylene tubular hydrogen bubble forming implement (e-3) without being covered by a cover material. The selective hydrogen adding equipment for living organism applicable fluid according to the present invention was obtained by dropping 500 mg of Fujisawa city tap water (generating-purpose water) into the hydrogen bubble forming implement, and closing the opening of the hydrogen bubble forming implement with a gas-permeable film (Monotoran Film, Type No.: FP10-01105-100, Nac Corporation) as the gas/liquid separating section (e-4).

Subsequently, a PET bottle for carbonated drink (about 530 cc volume when filled with full water to the mouth) was substantially filled with about 515 cc of clarified water (charcoal-treated water obtained by treating Fujisawa city tap water to pass through a charcoal column), and the selective hydrogen adding equipment for living organism applicable fluid was then disposed into the clarified water in the PET bottle.

The bottle was closed with its cap and left during 5 minutes.

Thereafter, one of the present inventors (Japanese man of 30's having an average physical size) held the middle portion of the PET bottle by his dominant hand and moved only the wrist to shake it such that the cap was forming into an arch above the wrist with a pace of 2 strokes per second, total 120 strokes (total 60 seconds).

Then, DH concentration was measured.

As shown in Tables 4 and 5, Examples 11 to 17 and Comparative Examples 2 and 3 are satisfactory as for DH concentration. However, when measuring the temperature of metal raw materials by the "metal raw material heat generation temperature measurement method", Examples 11 to 17 use metal raw materials of which the exothermic reaction is moderate or less, i.e. the temperature thereof is below 50 degrees (Examples 14 to 17) or the metal raw materials require 5 seconds or more before reaching 50 degrees C. if exceeding 50 degrees C. (Examples 11 to 13), whereas Comparative Examples 2 and 3 use metal raw materials of which the exothermic reaction is severe such that 50 degrees C. are reached within 5 seconds. Therefore, it can be said that a configuration suitable for the selective hydrogen adding equipment for living organism applicable fluid according to the present invention is of Embodiments 11 to 17 rather than Comparative Example 2 and 3.

DESCRIPTION OF REFERENCE NUMERALS a . . . valve
   a-1 . . . lampshade-like head part
   a-2 . . . axial part
   a-3 . . . flange
b . . . recessed component
   b-1 . . . center hole
   b-2 . . . fan-like hole
   b-3 . . . edge

What is claimed is:

1. A selective hydrogen adding equipment for supplying hydrogen to a living organism applicable fluid, comprising:
a hydrogen generating system that contains a hydrogen generating agent as an essential component;
a cover material that covers the hydrogen generating system;
a hydrogen bubble forming implement that stores the cover material that covers the hydrogen generating system and has a gas/liquid separating section; and
a closed container to accommodate the hydrogen adding equipment and a living organism applicable fluid,
wherein the gas/liquid separating section vents hydrogen gas generated by a contact reaction between the hydrogen generating agent and water or water vapor, the gas/liquid separating section avoids the water from flowing out and/or avoids the living organism applicable fluid from flowing in.

2. The selective hydrogen adding equipment as set forth in claim 1, wherein the gas/liquid separating section is characterized by comprising a valve or a gas permeable film.

3. A selective hydrogen adding equipment for supplying hydrogen to a living organism applicable fluid, comprising:
a hydrogen generating system that contains a hydrogen generating agent as an essential component;
a cover material that covers the hydrogen generating system;
a hydrogen bubble forming implement has a hydrogen generating cell that stores the cover material that covers the hydrogen generating system and has a gas/liquid separating section; and
a closed container to accommodate the hydrogen adding equipment and a living organism applicable fluid,
wherein the gas/liquid separating section vents hydrogen gas generated by a contact reaction between the hydrogen generating agent and water or water vapor, the gas/liquid separating section avoids flowing out of the water from the hydrogen generating cell to the closed container and/or avoids flowing in of the living organism applicable fluid from the closed container to the hydrogen generating cell.

4. The selective hydrogen adding equipment as set forth in claim 3, wherein the gas/liquid separating section is inserted in the hydrogen bubble forming implement, and the interior of hydrogen bubble forming implement has a two-cells structure with the gas/liquid separating section as the boundary.

5. The selective hydrogen adding equipment as set forth in claim 4, wherein one of the two-cells structure is the hydrogen generating cell accommodating the hydrogen generating agent and the other is the hydrogen supplying cell which supplies hydrogen gas to the living organism applicable fluid.

6. The selective hydrogen adding equipment as set forth in claim 4, wherein a hydrogen gas permeable hole is provided on the hydrogen supplying cell side wall of the hydrogen bubble forming implement.

7. The selective hydrogen adding equipment as set forth in claim 6, wherein the hydrogen supplying cell stores liquid.

* * * * *